US007314609B2

(12) United States Patent
Elmaleh

(10) Patent No.: US 7,314,609 B2
(45) Date of Patent: *Jan. 1, 2008

(54) STEREOISOMERS OF FATTY ACID ANALOGS FOR DIAGNOSTIC IMAGING

(75) Inventor: David R. Elmaleh, Newton, MA (US)

(73) Assignee: Molecular Insight Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/274,505

(22) Filed: Nov. 16, 2005

(65) Prior Publication Data

US 2006/0078495 A1   Apr. 13, 2006

Related U.S. Application Data

(63) Continuation of application No. 10/429,416, filed on May 5, 2003, now Pat. No. 7,005,119, which is a continuation of application No. 09/077,490, filed as application No. PCT/US96/19024 on Nov. 25, 1996, now abandoned.

(60) Provisional application No. 60/007,863, filed on Dec. 1, 1995.

(51) Int. Cl.
A61K 51/00 (2006.01)
A61M 36/14 (2006.01)

(52) U.S. Cl. .................. 424/1.89; 424/1.11; 424/1.65; 424/1.73; 424/1.81; 424/1.85; 424/9.1

(58) Field of Classification Search .............. 424/1.11, 424/1.65, 1.73, 1.81, 1.85, 9.1, 9.3, 9.4, 9.5, 424/9.6, 9.7, 9.8, 1.89; 562/606
See application file for complete search history.

(56) References Cited

U.S. PATENT DOCUMENTS

| 3,716,631 A | 2/1973 | Steggerda et al. |
| 4,323,547 A | 4/1982 | Knust et al. |
| 4,473,544 A | 9/1984 | Machulla et al. |
| 4,476,106 A | 10/1984 | Bardy et al. |
| 4,524,059 A | 6/1985 | Elmaleh et al. |
| 4,746,505 A | 5/1988 | Jones et al. |
| 4,764,358 A | 8/1988 | Knapp, Jr. et al. |
| 4,877,599 A | 10/1989 | Lees |
| 5,021,220 A | 6/1991 | Mertens |
| 5,370,860 A | 12/1994 | Elgavish et al. |
| 5,976,496 A * | 11/1999 | Dean et al. ................. 424/1.69 |
| 7,005,119 B2 * | 2/2006 | Elmalch ..................... 424/1.69 |
| 2003/0215386 A1 | 11/2003 | Elmalch |

OTHER PUBLICATIONS

Caveliers et al., "Intra-Individual Comparison of 3(R)-BMIPP and 3(S)-BMIPP Isomers in Humans", Oct. 1998, pp. 1672-1675, The Journal of Nuclear Medicine, vol. 39, No. 10.
Chang et al; "The Effect of Methyl Palmoxirate on Incorporation of [$U_{14}C$] Palmitate Into Rat Brain", Neurochemical Research 19(9): 1217-1223, (1994).
Communal et al.; Can. J. Physiol. Pharmacol., vol. 72:1120-1126, (Oct. 1994).
Cravatt et al., "Chemical Characterization Of A Family Of Brain Lipids That Induce Sleep", Science, vol. 268: 1506-1509 (1995).
De Geeter et al. "Relationship between blood flow and fatty acid metabolism in subacute myocardial infartion: a stucy by means of Tc-Sestamibi and I-.beta.-methyl-iodo-phenyl pentadecanoic acid," Eur. J. Nucl. Med 21: 283-291, 1994.
Elmaleh et al., "Corporation of $^{11}C$ and $^{14}C$-Labeled Fatty Acids And Their β-Methyl Analogs", Int. J. Nucl. Med. Biol. vol. 10, No. 4: 181-187 (1983).
Elmaleh et al., "Myocardial Extraction of 1-[$^{11}C$] Betamethylheptadecanoic Acid", The Journal of Nuclear Medicine, vol. 35, No. 3: 496-503 (1994).
Franken et al., A. "Abnormal Free Fatty Acid Uptake in Subacute Myocardial Infarction After Coronary Thrombolysis: Correlation with Wall Motion and Inotropic Reserve,".J. Nucl. Med. 35: 1758-1765, 1994.
Goodman et al., "Synthesis and Evaluation of Radioiodinated Terminal p-Iodophenyl-Substituted .alpha.- and β-Methyl-Branched Fatty Acids," J. Med. Chem., 27:390-397 (1984).
Lin et al., "Effects of Configuration on the Myocardial Uptake of Radioiodinated 3(R)-BMIPP and 3(S)-BMIPP in Rats," J Nucl. Med. 38:1434-1440, 1997.
Livni et al., "Beta-methyl[1-$^{11}C$] heptadecanoic Acid: A New Myocardial Metabolic Tracer For Positron Emission Tomography", The Journal of Nuclear Medicine, vol. 23, No. 2: 169-175 (1982).

(Continued)

Primary Examiner—Dameron L. Jones
(74) Attorney, Agent, or Firm—Gilberto M. Villacorta; Jeffrey R. Lomprey; Foley & Lardner LLP

(57) ABSTRACT

The present invention provides novel imaging agents for clinical diagnosis of injuries and diseases, in the form of a radionuclide in spatial proximity to a substantially pure stereoisomer of a fatty acid analog. The invention also provides methods for using the novel imaging agents, and kits containing one or more of the novel imaging agents of the invention.

11 Claims, No Drawings

OTHER PUBLICATIONS

Fischman et al., "Myocardial Fatty Acid Imaging: Rationale, Comparison of $^{11}$C- and $^{123}$I-Labeled Fatty Acids, and Potential Clinical Utility", American Journal of Cardiac Imaging, vol. 3, No. 4: 288-296 (1989).

Gatley et al., "On the rate-limiting step in myocardial clearance of label from 16-iodohexadecanoic acid," J. Nucl. Med. 24: P12, 1983 (abstr.).

Goodman et al., "New Myocardial Imaging Agents: Synthesis of 15-(p-Iodophenyl)-3(R,S)- methylpentadecanoic Acid by Decomposition of a 3,3-(1,5-Pentanediyl) triazene Precursor", The Journal of Organic Chemistry, vol. 49, No. 13: 2322-2325 (1984).

Jones Jr., et al., "Synthesis and Biodistributionof a New $^{99}$mTechnetium Fatty Acid", Nuclear Medical Biology, vol. 21, No. 1: 117-123 (1994).

Kairento et al., "Comparative Evaluation of [$^{123}$I]4-p-Iodophenyl-Beta-Methyltetradecanoic Acid and Thallium-201 in the Detection of Infarcted Areas in the Dog Heart Using SPECT", Nuclear Medical Biology, vol. 15, No. 3:333-338 (1988).

Knapp, Jr. "Myocardial Metabolism of Radioiodinated BMIPP", The Journal of Nuclear Medicine, vol. 36, No. 6: 1051-1054 (1995).

Kropp et al., "Evaluation of ischemia and myocardial viability in patients with coronary artery disease (CAD) with iodine-123 labeled 15-(p-iodophenyl)-3-R,S-methylpentadecanoic acid (BMIPP)," BMIPP. Ann Nucl Med 7: 93-100, 1993.

Lin et al., "Effects of Configuration on the Myocardial Uptake of Radioiodinated 3(R)-BMIPP and 3(S)-BMIPP in Rats", Sep. 1997, pp. 1434-1441, The Journal of Nuclear Medicine, vol. 38, No. 9.

Machulla et al, "Comparative Evaluation of Fatty Acids Labeled with C-11, C1-34m, Br-77 and I-123 for Metabolic Studies of the Myocardium: Concise Communication," J. Nucl. Med. 19:298-302, 1978.

Mertens et al.; European Journal Of Nuclear Medicine, vol. 13(3): 159-160, (1987).

Miller et al., "Fatty Acid Analogue Accumulation: A Marker of Myocyte Viability in Ischemic-Reperfused Myocardium" Circulation Research, vol. 63, No. 4: 681-692 (1988).

Most et al., "Free Fatty Acid Metabolism of the Human Heart at Rest," J. Clin. Invest. 48:1177-1188, 1969.

Nakai et al., "Serial Course of Left Ventricular Function, Perfusion and Fatty Acid Uptake in the Cardiomyopathic Hamster", The Journal of Nuclear Medicine, vol. 34, No. 8: 1309-1315 (1993).

Nariai et al.; "In Vivo Incorporation of[9,10$_{3H}$]- Palmitate Into a Rat Metastatic Brain-Tumor Model", J. Neurosurg. 74: 643-649, (1991).

Naruse et al.; Kakuigaku, 29(1): 77-84 (1992).

Neely et al., Myocardial Utilization of Carbohydrates and Lipids, Progr. Cardiovasc. Res. 15:289-329, 1972.

Neely et al., "Relationship Between Carbohydrate and Lipid Metabolism and the Energy Balance of Heart Muscle," Ann. Rev. Physiol. 36: 413-459, 1974.

Okada et al., "Myocardial Kinetics of $^{123}$1-Labeled-16-Hexadecanoic Acid", European Journal of Nuclear Medicine, vol. 8: 211-217 (1983).

Opie, "Metabolism of the heart in health and disease," Am. Heart J. 76: 685-698, 1968.

Poe, Robinson GD Jr., MacDonald NS, "Myocardial Extraction of Labeled Long-Chain Fatty Acid Analogs," Proc. Soc. Exp. Biol. Med 148:215-218, 1975.

Takahashi et al.; "Synthesis of 1- $^{11}$C-Labeled Fatty Acid From [$^{11}$C]HCN", Appl. Radiat. Isot. 41(7); 649-654, (1990).

Saito et al., "Differentiation of Regional Perfusion And Fatty Acid Uptake In Zones Of Myocardial Injury", Nuclear Medicine Communications, vol. 12: 663-675 (1991).

Schon, et al, "C-11 palmitic acid for the noninvasive evaluation of regional fatty acid metabolism with positron-computed tomography," Am. Heart J. 103: 532-561, 1982.

Schon et al, "Measurement of Myocardial Fatty Acid Metabolism: Kinetics of Iodine-123 Heptadecanoic Acid in Normal Dog hearts," J. Nucl. Med. 27: 1449-1455, 1986.

Solomons, "Fatty Acids and Glyceryl Trialkanoates", Organic Chemistry, Fourth Edition, pp. 1039-1043 (1988).

Takeishi et al.; Annals of Nuclear Medicine, 9(3): 125-130, (Aug. 1995).

Wakasugi et al., "Myocardial Utilization And Left Ventricular Function In Adrianmycin Caryomyopathy", The Journal of Nuclear Medicine, vol. 34, No. 9: 1529-1535 (1993).

Yamamoto et al., "Dual Tracer Autoradiographic Study of β-Methyl-(1$^{14}$C) Heptadecanoic Acid and 15-p-($^{13}$1I)-Iodophenyl-.beta.-Methylpentadecanoic Acid In Normaotensive and Hypertensive Rats", The Journal of Nuclear Medicine, vol. 27, No. 7: 1178-1183 (1986).

Yonekura et al., "Regional Myocardial Substrate Uptake in Hypertensive Rats: A Quantitative Autoradiographic Measurement", Science, vol. 227: 1494-1496 (1985).

Zierler, "Fatty Acids as Substrates for Heart and Skeletal Muscle," Circ. Res. 38: 459-463, 1976.

* cited by examiner

STEREOISOMERS OF FATTY ACID ANALOGS FOR DIAGNOSTIC IMAGING

CROSS REFERENCE TO RELATED APPLICATIONS

This application is a Continuation of U.S. Utility application Ser. No. 10/429,416, filed May 5, 2003 now U.S. Pat. No. 7,005,119, which is a Continuation of U.S. application Utility Ser. No. 09/077,490, filed May 29, 1998, now abandoned, filed as 371 of International Application No. PCT/US96/19024, filed on Nov. 25, 1996, which in turn claims priority to U.S. Provisional Application No. 60/007,863, filed on Dec. 1, 1995.

GOVERNMENT INTERESTS

This invention was made with Government support from the National Institutes of Health. The Government has certain rights in the invention.

DESCRIPTION

The present invention relates to the field of nuclear medicine. More specifically, the invention relates to diagnostic imaging using substantially pure stereoisomers of radionuclide-containing fatty acid analogs.

BACKGROUND OF THE INVENTION

Clinical imaging technology plays a significant role in diagnosis of injuries and disease processes. Virtually any part of an animal's body can now be examined for diagnostic purposes using a variety of imaging techniques. Radiography has long been used to image body parts through which externally generated x-rays are transmitted. Computerized axial tomography (CAT) provides cross-sectional x-ray images of a plane of the body. Specific tissues or organs may be targeted in positron emission tomography (PET), single photon emission computed tomography (SPECT), and scintigraphy. In PET, SPECT, and scintigraphy, radiopharmaceutical agents capable of sequestering to some degree in the target tissue or organ are internally administered to the patient, and images are generated by detecting the radioactive emissions from the sequestered radiopharmaceutical agent. Radiopharmaceutical agents include nuclides such as $^{201}Tl$, $^{99m}Tc$, $^{133}Xe$, and the like; chelates of nuclides; nuclide labeled metabolic agents such as $^{11}C$-deoxy-D-glucose, $^{18}F$-2-fluorodeoxy-D-glucose, [1-$^{11}C$]- and [$^{123}I$]β-methyl fatty acid analogs, $^{13}N$-ammonia, and the like; infarct avid agents such as $^{99m}Tc$-tetracycline, $^{99m}Tc$-pyrophosphate, $^{203}Hg$-mercurials, $^{67}Ga$-citrate, and the like; and nuclide labeled monoclonal antibodies. Whole cells such as erythrocytes and leukocytes may also be labeled with a radionuclide and function as radiopharmaceutical agents.

The amount and type of clinical information that can be derived from PET, SPECT, and scintigraphic images is related in part to the ability of the radiopharmaceutical agent to sequester in the target tissue or organ. Although many radiopharmaceuticals are available for clinical use, for a given imaging instrument, the agents generally have limitations in the resolution of the image generated. The resolution available for a particular imaging agent is highly dependent on the affinity of the radiopharmaceutical to bind at the site of injury as compared to the affinity of the radiopharmaceutical to bind to healthy tissue surrounding the site of injury.

In spite of their limitations, radiopharmaceuticals are used in a variety of types of studies to obtain different kinds of information. For example, radiopharmaceutical agents used in cardiac blood flow and blood pool studies provide information on murmurs, cyanotic heart disease, and ischemic heart disease. Perfusion scintigraphy agents provide measurements of blood flow useful in detection of coronary artery disease, assessment of pathology after coronary arteriography, pre- and postoperative assessment of coronary artery disease, and detection of acute myocardial infarction. Infarct avid agents are used for "hot spot" infarct imaging. Radiopharmaceuticals which allow binding to specific cardiac receptors, while generally still in the developmental stage, may allow detection of highly specific binding in the cardiovascular system. Radionuclide-containing antibodies directed against the heavy chain of cardiac myosin have been proposed to identify zones of acute myocardial necrosis, and $^{99m}Tc$-labeled low density lipoprotein may be useful to detect atheromatous lesions in their early stages after onset of endothelial damage. $^{99m}Tc$-HMPO and $^{123}I$-iodo-amphetamines are used to study changes in brain blood flow with SPECT. Receptor-ligand interactions, glucose utilization, protein synthesis, and other physiological parameters are also studied with other radiopharmaceuticals using PET.

Radiopharmaceutical agents capable of detecting the rate and amount of metabolism are particularly important to the progress of clinical nuclear medicine, since they allow studies of the energy consumption in the various stages of disease processes. For example, cardiac metabolism can now be studied using labeled physiologic tracers and using analogs of "natural" metabolites that are transported in the same manner as the metabolite but go through only a few reactions of the metabolic pathway and are then trapped in the tissue in a chemically known form. The glucose analog [$^{18}F$]-2-fluoro-2-deoxy-D-glucose can be used to detect areas of altered glucose metabolism in the heart or other target organs which may be associated with hypoxia and anoxia and thus aid in defining the extent of an ischemic injury or cardiomyopathy. Fatty acids are the main source of energy for the heart, and radiolabeled fatty acids or their close analogs have been used to study heart metabolic integrity. β-methyl-fatty acid analogs are one group of fatty acids used as metabolic tracers.

Racemic mixtures of many β-methyl-fatty acid analogs are disclosed in U.S. Pat. No. 4,524,059. One β-methyl-fatty acid analog, [$^{123}I$]-15-(p-iodophenyl)-3-R,S-methylpentadecanoic acid ([$^{123}I$]-BMIPP) has been used for myocardial imaging in Japan. However, the racemic nature of [$^{123}I$]-BMIPP makes it less than optimal for imaging studies, since uptake and metabolism of the R and S stereoisomers may differ and thus decrease the specificity of the reagent for heart tissue. Although use of stereoisomers of β-methyl-fatty acid analogs has been suggested, obtaining such isomers at a meaningful level of purity has been difficult.

Because an accurate imaging diagnosis of injury or disease depends so heavily on the agent used, a need continues to exist for radiopharmaceuticals with improved tissue and organ specificity.

SUMMARY OF THE INVENTION

The present invention provides improved and novel radiopharmaceutical agents for diagnostic imaging of injuries and disease states. The imaging agents of the invention are radionuclide-containing analogs of fatty acids and are particularly suitable for cardiovascular and brain imaging.

The imaging agents of the invention are substantially pure stereoisomers of fatty acid analogs.

In one embodiment, the invention provides an imaging agent comprising a radionuclide in spatial proximity to a stereoisomer of more than 75% isomeric purity of a fatty acid analog having the formula

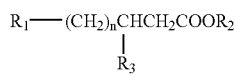

wherein $R_1$ is selected from the group consisting of a hydrogen, fluorine, an iodoaryl group, an iodoallyl group, and an iodothiophene group; $R_2$ is selected from the group consisting of a hydrogen, a primary amine, a secondary amine, a tertiary amine, an alkyl group, a substituted alkyl group, an aryl group, and a substituted aryl group; $R_3$ is selected from the group consisting of a hydrogen, a methyl, a hydroxyl, a keto ester, a methoxy, a halide, and an amine; and n is greater than 12.

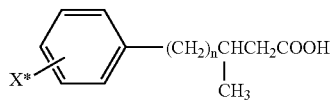

In another embodiment the invention provides an analog of the formula wherein X* is a radioactive isotope of a halogen and n is an integer between 9 and 17, inclusive.

In another embodiment, the invention provides an imaging agent comprising a radionuclide in spatial proximity to an isomer of a fatty acid analog having the formula

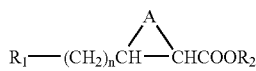

wherein $R_1$ is selected from the group consisting of a hydrogen, fluorine, an aryl group, a substituted aryl group, an allyl group, a substituted allyl group, a vinyl group, a substituted vinyl group, and an iodothiophene group; $R_2$ is selected from the group consisting of a hydrogen, a primary amine, a secondary amine, a tertiary amine, an alkyl group, a substituted alkyl group, an aryl group, and a substituted aryl group; A is selected from the group consisting of a methylene group, an ethylene group, an oxygen, a sulfur, and a nitrogen; and n is greater than 10.

In another embodiment, the invention provides an imaging agent comprising a radionuclide in spatial proximity to a stereoisomer of a fatty acid analog having the formula

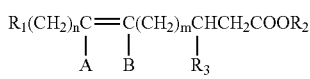

wherein $R_1$ is selected from the group consisting of a hydrogen, fluorine, an aryl group, a substituted aryl group, an allyl group, a substituted allyl group, a vinyl group, a substituted vinyl group, and an iodothiophene group; $R_2$ is selected from the group consisting of a hydrogen, a primary amine, a secondary amine, a tertiary amine, an alkyl group, a substituted alkyl group, an aryl group, and a substituted aryl group; $R_3$ is selected from the group consisting of a hydrogen, a methyl, a hydroxyl, a keto ester, a methoxy, a halide, and an amine; A is selected from the group consisting of a hydrogen, an alkyl group, and a halide; B is selected from the group consisting of a hydrogen, an alkyl group, and a halide; n is greater than 3; and m is greater than 3.

In another embodiment, the invention provides a method of imaging cardiovascular or brain tissue in a mammal which comprises administering to the mammal an imaging agent comprising a radionuclide in spatial proximity to an isomer of a fatty acid analog, and detecting the spatial distribution of the agent accumulated in the mammal.

In another embodiment, the invention provides a method of detecting a cardiovascular lesion in a mammal which comprises administering to the mammal an imaging agent comprising a radionuclide in spatial proximity to an isomer of a fatty acid analog, and detecting the spatial distribution of the agent accumulated in the mammal's cardiovascular system, wherein a detected accumulation of agent in a region which is different from the detected accumulation of agent in other regions is indicative of a lesion.

In another embodiment, the invention provides a method of detecting a brain lesion in a mammal which comprises administering to the mammal an imaging agent comprising a radionuclide in spatial proximity to an isomer of a fatty acid analog, and detecting the spatial distribution of the agent accumulated in the mammal's brain, wherein a detected accumulation of agent in a region which is different from the detected accumulation of agent in other regions is indicative of a lesion.

In another embodiment, the invention provides a kit for imaging which comprises at least one imaging agent comprising a radionuclide in spatial proximity to an isomer of a fatty acid analog, and a pharmaceutically acceptable carrier.

In another embodiment, the invention provides a kit for imaging which comprises at least one stereoisomer of a fatty acid analog in combination with a chelating agent, and a pharmaceutically acceptable carrier.

DETAILED DESCRIPTION OF THE PREFERRED EMBODIMENTS

The patent and scientific literature referred to herein establishes the knowledge that is available to those with skill in the art. The issued U.S. patents and allowed applications cited herein are hereby incorporated by reference.

The present invention provides imaging agents which generally comprise a radionuclide in spatial proximity to a substantially pure stereoisomer of a fatty acid analog. In accordance with the invention, spatial proximity between the nuclide and the stereoisomer may be effected in any manner which preserves the specificity of the stereoisomer for its target tissue. For example, spatial proximity between the nuclide and the stereoisomer may be effected by a covalent or non-covalent chemical bond. Such a chemical bond may be affected through a chelating substance or an auxiliary molecule. Alternatively, spatial proximity between the nuclide and the stereoisomer may be effected by incorporating the nuclide and the stereoisomer in a micelle or liposome, in such a way that the affinity of the stereoisomer for its target tissue is maintained. Spatial proximity between the nuclide and the stereoisomer may also be effected by attaching the nuclide and the stereoisomer to a matrix such as a microsphere.

As defined herein a "substantially" pure stereoisomer is one containing more than 75% of a single stereoisomer of fatty acid analog. Preferably, the substantially pure stereoisomer of the invention contains more than 75% of a single stereoisomer of a fatty acid analog. More preferably, the substantially pure stereoisomer of the invention contains more than 80% of a single stereoisomer of a fatty acid analog. Most preferably, the substantially pure stereoisomer of the invention contains more than 85% of a single stereoisomer of a fatty acid analog.

In one embodiment, the imaging agent of the invention comprises a radionuclide in spatial proximity to a stereoisomer of more than 75% isomeric purity of a β-methyl (or 2-methyl) fatty acid analog having the formula

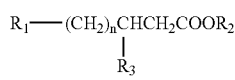

wherein $R_1$ is selected from the group consisting of a hydrogen, fluorine, an iodoaryl group, an iodoallyl group, and an iodothiophene group; $R_2$ is selected from the group consisting of a hydrogen, a primary amine, a secondary amine, a tertiary amine, an alkyl group, a substituted alkyl group, an aryl group, and a substituted aryl group; $R_3$ is selected from the group consisting of a hydrogen, a methyl, a hydroxyl, a keto ester, a methoxy, a halide, and an amine and n is greater than 12. In this embodiment, the stereoisomer may be an R-stereoisomer or an S-stereoisomer. This embodiment encompasses stereoisomers having the formula as shown, where $R_3$ is bonded at the C3 position as shown, and in addition encompasses aliphatic fatty acid analogs having similar formulae but in which $R_3$ is bonded to other carbon moieties of the fatty acid chain. For example, $R_3$ may be bonded at the C5, C7, or C9 position of the aliphatic fatty acid chain, counting from the carboxyl carbon. Racemic mixtures of such fatty acid analogs are disclosed in U.S. Pat. No. 4,524,059.

The chemical nature, as well as the size of any substituent can affect the properties of the analog. Generally, an analog having a substituent which does not render the analog excessively polar, e.g., an unsubstituted alkyl group, is taken up primarily by the heart, while an analog containing a polar group, e.g., an ether, or alcohol, will be taken up primarily by the liver.

The chain length of the analog also affects the tissue by which it is primarily taken up. Generally, a chain length of 12-20 carbon atoms, inclusive, is optimal for selective uptake by myocardial tissue, while a chain length of 5 to 11 carbon atoms inclusive will be preferred for selective uptake by the liver. The carbon chain of the analog can be saturated or unsaturated.

The chain length can vary widely. The nature and position of any radioactive label can also be varied. $^{11}C$ or $^{14}C$ is preferably placed at the carboxylic position for convenience in synthesis, although in theory this radioactive isotope could appear at any position on the chain, as well as on the substituent. Rather than using an isotope of carbon, a radioactive halogen isotope (e.g., $^{18}F$, $^{34}Cl$, $^{75}Br$, $^{76}Br$, $^{77}Br$, $^{123}I$, or $^{131}I$) can be substituted at any position along the chain to provide a radioactive label. To prevent enzymatic dehalogenation, the halogen label can advantageously be included either in a substituted phenyl group or as a terminal transvinyl iodide group. In the beta-position, the halogenated phenyl group would serve both as radioactive label and as oxidation inhibitor.

Variation in the chain length of the analog, the nature and position of any radioactive label, and the nature and position of organic substituents will of course dictate concomitant variations in the synthesis of the analogs of the invention.

Stereoisomers of β-methyl fatty acid analogs having greater than 75% purity as defined above may be prepared using any of the synthetic schemes set forth below. In general, the stereoisomers of the invention may be prepared using an asymmetric synthesis combined with final chromatographic separation on an optically active support or an optically active element, as indicated in Schemes 1 and 2. Alternatively, stereoisomers of the starting materials may be separated using known methods, and synthesis of the stereoisomer of the invention may be completed without changing the configuration of the optically active moiety. All precursors, intermediates, and final products of the syntheses may optionally be subjected to additional asymmetric chromatographic separations, to increase the stereoisometric purity of the fatty acid analog.

An Asymmetric Synthesis of an R-3-methylfatty Acid

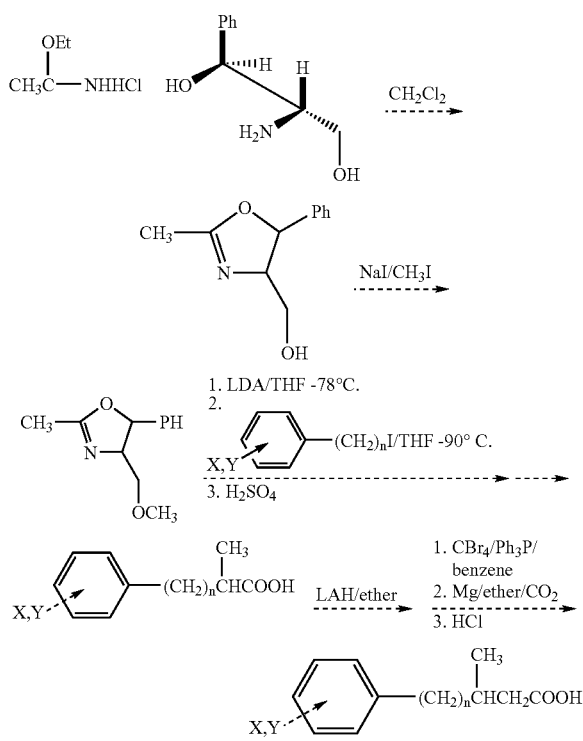

X, Y=any combination of H, halogen, alkyl, aryl, acyl, alkoxy, $SnBu_3$-diazonium-, triazine- The final optically active product could be further enriched by asymetric chromatographic methods.

An Asymmetric Synthesis of an S-3-methylfatty Acid

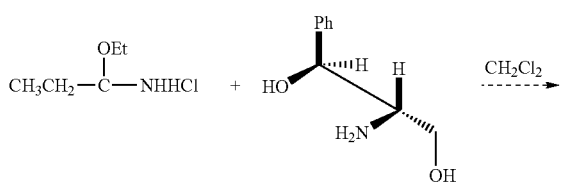

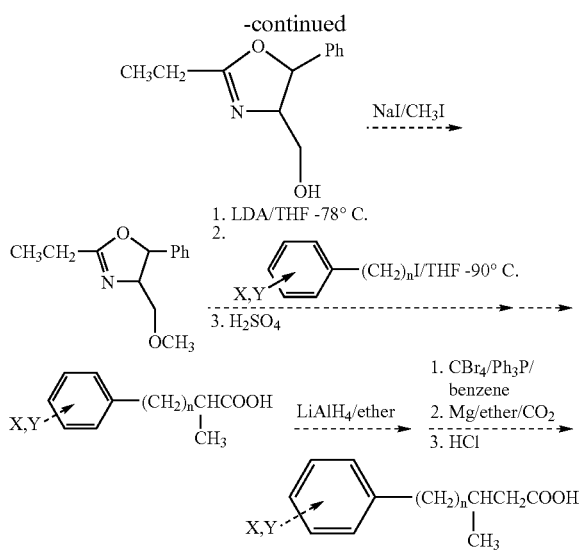

X, Y=any combination of H, halogen, alkyl, aryl, acyl, alkoxy, SnBu$_3$-diazonium-, triazine- The final optically active product could be further enriched by asymetric chromatographic methods.

LDA=lithium diisopropyl amido THF=tetrahydrofuran

An Alternative Synthesis for R or S 3-methyl Substituted Fatty Acids

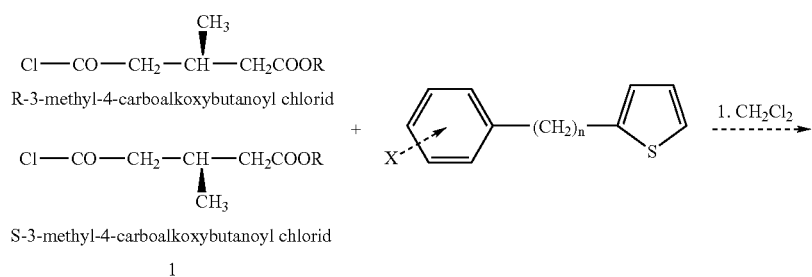

X=halogen, alkyl, aryl, acyl, SnBu$_3$-, diazonium-, triazine-

In this scheme the synthesis and separation of the optical isomers of precursor 1 is performed prior to the chemical synthesis of the final fatty acid 2. The optical isomers of 2 could be further enriched by asymetric chromatographic methods.

The invention is also embodied as an imaging agent comprising a radionuclide in spatial proximity to a stereoisomer of an α,β-substituted (or 2,3-substituted) fatty acid analog having the formula

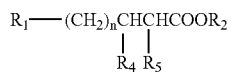

wherein $R_1$ is selected from the group consisting of a hydrogen, a fluorine, an iodoaryl group, an iodoallyl group and an iodothiophene group; $R_2$ is selected from the group consisting of a hydrogen, a primary amine, a secondary amine, a tertiary amine, an alkyl group, a substituted alkyl group, an aryl group, and a substituted aryl group; $R_4$ is an alkyl-group; $R_5$ is an alkyl group; and n is greater than 12. In this embodiment, the imaging agent may be a 2S,3S-stereoisomer, a 2S,3R-stereoisomer, a 2R,3R-stereoisomer, or a 2R,3S-stereoisomer. Stereoisomers of α,β-substituted fatty acid analogs having greater than 75% purity as defined above may be prepared using modifications of synthetic schemes 1-3, wherein a hydrogen of the α-carbon is substituted with an $R_4$ moiety.

The invention may also be embodied as an imaging agent comprising a radionuclide in spatial proximity to an isomer of a fatty acid analog having the formula

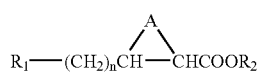

wherein $R_1$ is selected from the group consisting of a hydrogen, a fluorine, an aryl group, a substituted aryl group, an allyl group, a substituted allyl group, a vinyl group, a substituted vinyl group, and an iodothiophene group; $R_2$ is selected from the group consisting of a hydrogen, a primary amine, a secondary amine, a tertiary amine, an alkyl group, a substituted alkyl group, an aryl group, and a substituted aryl group; A is selected from the group consisting of a methylene group, an ethylene group, an oxygen, a sulfur, and a nitrogen; and n is greater than 10. The imaging agent of this embodiment may be prepared according to the synthetic scheme set forth below.

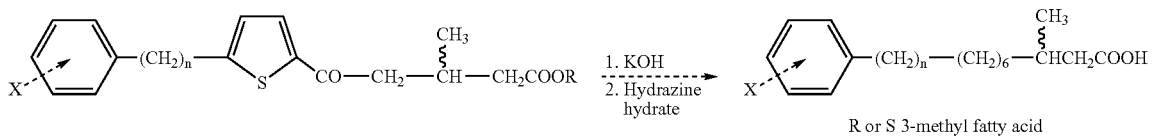

Synthesis of Oxiranyl Fatty Acids

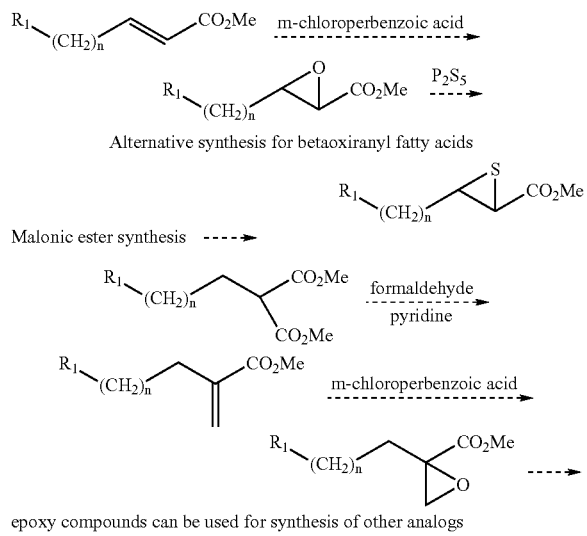

epoxy compounds can be used for synthesis of other analogs

The invention is further embodied as an imaging agent comprising a radionuclide in spatial proximity to a stereoisomer of a fatty acid analog having the formula

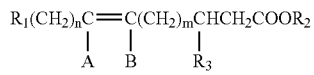

wherein $R_1$ is selected from the group consisting of a hydrogen, a fluorine, an aryl group, a substituted aryl group, an allyl group, a substituted allyl group, a vinyl group, a substituted vinyl group, and an iodothiophene group; $R_2$ is selected from the group consisting of a hydrogen, a primary amine, a secondary amine, a tertiary amine, an alkyl group, a substituted alkyl group, an aryl group, and a substituted aryl group; $R_3$ is selected from the group consisting of a hydrogen, a methyl, a hydroxyl, a keto ester, a methoxy, a halide, and an amine; A is selected from the group consisting of a hydrogen, an alkyl group, and a halide; B is selected from the group consisting of a hydrogen, an alkyl group, and a halide; n is greater than 3; and m is greater than 3. In this embodiment, the stereoisomer may be an R, cis-stereoisomer, an R, trans-stereoisomer, an S, cis-stereoisomer, or an S, trans-stereoisomer. Stereoisomers having greater than 75% purity as defined above may be prepared using the synthetic scheme set forth below.

Synthesis of Monounsaturated Fatty Acids

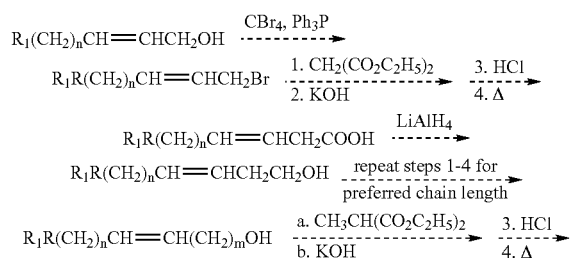

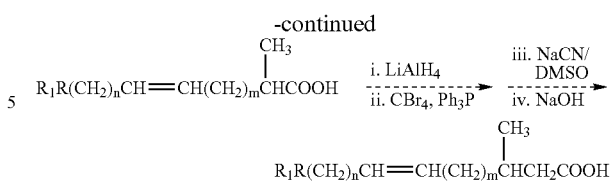

The imaging agents described above may contain any radionuclide in accordance with the invention. Preferably, the imaging agents of the invention contain radionuclides suitable for use in PET or SPECT imaging. More preferably, the imaging agent of the invention contains a radionuclide selected from the group consisting of $^{123}I$, $^{99m}Tc$, $^{18}F$, $^{68}Ga$, $^{62}Cu$, $^{111}In$, and the like. Such radionuclides may be incorporated into the imaging agent by covalent bonding directly to an atom of the fatty acid moiety, or the radionuclide may be non-covalently or covalently associated with the fatty acid moiety through a chelating structure. Any suitable chelating structure may be used to provide the covalent or non-covalent association between the radionuclide and the fatty acid moiety of the agent. Many such chelating structures are known in the art. Preferably, the chelating structure is selected from the group consisting of an $N_2S_2$ structure, an $N_4$ structure, an isonitrile, a hydrazine, a HYNIC (hydrazinonicotinic acid) group, a phosphorus containing group, and the like. The chelating structure may be covalently or non-covalently associated with any moiety of the imaging agent. For example, the chelating structure may be associated with the $R_1$ moiety of the fatty acid analog, with the $R_2$ moiety of the fatty acid analog, or with the $(CH_2)_n$ moiety of the analog. In accordance with the invention, the stereoisomer of the fatty acid analog may be synthesized to contain a chelating group, or a chelating group may be added to the stereoisomer after synthesis.

When $^{123}I$ is the radionuclide, the fatty acid analog stereoisomer may be labeled in accordance with the general radioiodination protocol set forth below.

General Radioiodination Procedures

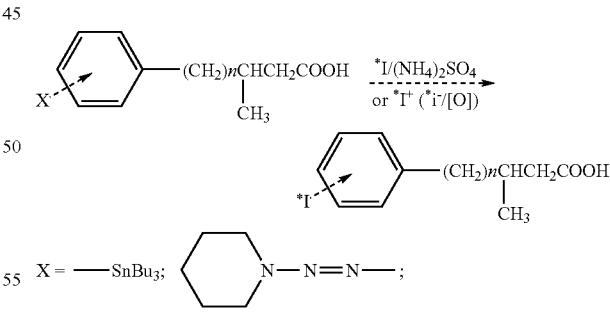

I - or other groups which could be exchanged by nucleophilic or electrophilic radioioidide(ine)

*I = $^{123, 125, 131}I$

Other methods for radioiodinating the stereoisomer may also be used, for example, Bolton-Hunter radioiodination, chloramine T radioiodination, and the like.

When the radionuclide is $^{99m}Tc$, the imaging agent may be labeled according to the general labeling protocol set forth below.

$^{99m}$Tc-radiolabeling of Fatty Acids

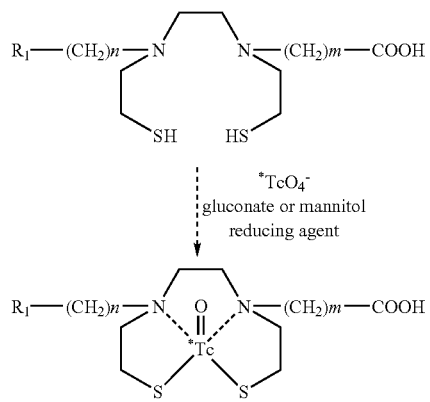

n=2-6: m=2-6
R=H, halogen, alkyl, aryl, acyl, alkoxy, allyl haloallyl
*Tc=$^{99m}$Tc
Other $N_2S_2$ fatty acid configurations are possible e.g.

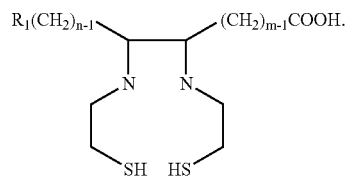

The cardiovascular imaging agents of the invention may be used in accordance with the methods of the invention by those of skill in the art, e.g., by specialists in nuclear medicine, to image cardiovascular or brain tissue in a mammal or to detect cardiovascular or brain lesions in a mammal. Some cardiovascular or brain lesions are evident when a dark spot appears within the image, for example, within a labeled heart or within a labeled brain, indicating the presence of necrotic tissue. Alternatively, a carcinomic lesion might be detectable as a brighter spot within the image, indicating a region of enhanced metabolism at the site of a tumor. A particularly useful imaging approach employs more than one imaging agent to perform simultaneous studies. For example, simultaneous studies of perfusion and metabolic function would allow study of coupling and uncoupling of flow and metabolism, thus facilitating determinations of tissue viability after a cardiac injury. Such determinations are useful in diagnosis of cardiac ischemia, cardiomyopathy, tissue viability, hybrinating heart, and other heart abnormalities.

The imaging agents of the invention are used in the following manner. An effective amount of the imaging agent (from 1 to 50 mCi) may be combined with a pharmaceutically acceptable carrier for use in imaging studies. In accordance with the invention, "an effective amount" of the imaging agent of the invention is defined as an amount sufficient to yield an acceptable image using equipment which is available for clinical use. An effective amount of the imaging agent of the invention may be administered in more than one injection. Effective amounts of the imaging agent of the invention will vary according to factors such as the degree of susceptibility of the individual, the age, sex, and weight of the individual, idiosyncratic responses of the individual and dosimetry. Effective amounts of the imaging agent of the invention will also vary according to instrument and film-related factors. Optimization of such factors is well within the level of skill in the art.

As used herein, "pharmaceutically acceptable carrier" includes any and all solvents, dispersion media, coatings, antibacterial and antifungal agents, isotonic agents, absorption delaying agents, and the like. The use of such media and agents for pharmaceutically active substances is well known in the art. The imaging agent of the invention may further be administered to an individual in an appropriate diluent or adjuvant, co-administered with enzyme inhibitors or in an appropriate carrier such as human serum albumin or liposomes. Supplementary active compounds can also be incorporated into the imaging agent of the invention. Pharmaceutically acceptable diluents include saline and aqueous buffer solutions. Adjuvants contemplated herein include resorcinols, non-ionic surfactants such as polyoxyethylene oleyl ether and n-hexadecyl polyethylene ether. Enzyme inhibitors include pancreatic trypsin inhibitor, diethylpyrocarbonate, and trasylol. Liposomes include water-in-oil-in-water CGF emulsions as well as conventional liposomes (Strejan et al. (1984) *J. Neuroimmunol.* 7, 27).

Preferably, the imaging agent of the invention is administered intravenously, and the imaging agent will be formulated as a sterile, pyrogen-free, parenterally acceptable aqueous solution. The preparation of such parenterally acceptable solutions, having due regard to pH, isotonicity, stability, and the like, is within the skill in the art. A preferred formulation for injection should contain, in addition to the cardiovascular imaging agent, an isotonic vehicle such as Sodium Chloride Injection, Ringer's Injection, Dextrose Injection, Dextrose and Sodium Chloride Injection, Lactated Ringer's Injection, or other vehicle as known in the art. The formulation used in the present invention may also contain stabilizers, preservatives, buffers, antioxidants, or other additives known to those of skill in the art.

The amount of imaging agent used for diagnostic purposes and the duration of the imaging study will depend upon the nature and severity of the condition being treated, on the nature of therapeutic treatments which the patient has undergone, and on the idiosyncratic responses of the patient. Ultimately, the attending physician will decide the amount of imaging agent to administer to each individual patient and the duration of the imaging study.

In another embodiment, the invention provides a kit for imaging which comprises one or more of the imaging agents described above, in combination with a pharmaceutically acceptable solution containing a carrier such as human serum albumin or an auxiliary molecule such as mannitol or gluconate. Human serum albumin for use in the kit of the invention may be made in any way, for example, through purification of the protein from human serum or through recombinant expression of a vector containing a gene encoding human serum albumin. Other substances may also be used as carriers in accordance with this embodiment of the invention, for example, detergents, dilute alcohols, carbohydrates, and the like. In one embodiment, a kit according to the invention may contain from about 1 to about 30 mCi of an imaging agent. In another embodiment, a kit may contain the unlabeled fatty acid stereoisomer which has been covalently or non-covalently combined with a chelating agent, and an auxiliary molecule such as mannitol, gluconate, and the like. The unlabeled fatty acid stereoisomer/chelating agent may be provided in solution or in lyophilized form. The radionuclide, for example, $^{99m}$Tc from a commercially available $^{99}$Mo/$^{99m}$Tc generator, is combined with the unlabeled fatty acid stereoisomer/chelating agent for a time and at a temperature sufficient to chelate the radionuclide to the fatty acid stereoisomer/chelating agent, and the imaging agent thus formed is injected into the patient. The kits of the invention may also include other components which facilitate practice of the methods of the invention. For example, buffers, syringes, film, instructions, and the like may optionally be included as components of the kits of the invention.

Although a few exemplary embodiments of this invention have been described in detail above, those skilled in the art will readily appreciate that many modifications are possible in the exemplary embodiments without materially departing from the novel teachings and advantages of this invention. For example, many other chemical groups are interchangeable with the various substituted moieties without significantly altering the activity of the stereoisometric fatty acid analog for diagnostic imaging purposes. Accordingly, all such modifications are intended to be included within the scope of this invention as defined in the following claims.

What is claimed is:

1. A substantially pure stereoisomer of 15-(p-radiohalophenyl)-3-methylpentadecanoic acid, in which radiohalo is selected from the group consisting of radioiodo and radiofluoro.

2. The substantially pure stereoisomer of claim 1, which is 15-(p-[$^{123}$I]iodophenyl)-3-(R)-methylpentadecanoic acid.

3. The substantially pure stereoisomer of claim 1, which is 15-(p-[$^{231}$I]iodophenyl)-3-(S)-methylpentadecanoic acid.

4. The substantially pure stereoisomer of claim 1, which 15-(p-[$^{18}$F]fluorophenyl)-3-(R)-methylpentadecanoic acid.

5. The substantially pure stereoisomer of claim 1, which 15-(p-[$^{18}$F]fluorophenyl)-3-(S)-methylpentadecanoic acid.

6. A method of radio imaging cardiovascular tissue of a subject comprising administering intravenously to a subject an effective amount of a substantially pure stereoisomer of a radionuclide labeled β-methyl fatty acid analog, which is 15-(p-radiohalophenyl)-3-methylpentadecanoic acid.

7. The method of claim 6 in which said β-methyl fatty acid analog is 15-(p-[$^{123}$I]iodophenyl)-3-methylpentadecanoic acid.

8. The method of claim 6 in which said β-methyl fatty acid analog is 15-(p-[$^{131}$I]iodophenyl)-3-methylpentadecanoic acid.

9. The method of claim 6 in which said β-methyl fatty acid analog is 15-(p-[$^{18}$F]fluorophenyl)-3-methylpentadecanoic acid.

10. The method of claim 6 in which said β-methyl fatty acid analog has an (R)-stereoisomeric configuration.

11. The method of claim 6 in which said β-methyl fatty acid analog has an (S)-stereoisomeric configuration.

* * * * *